United States Patent [19]
Daigle

[11] Patent Number: 5,127,409
[45] Date of Patent: Jul. 7, 1992

[54] ULTRASOUND DOPPLER POSITION SENSING

[76] Inventor: Ronald E. Daigle, 22126 NE. 62nd Pl., Redmond, Wash. 98053

[21] Appl. No.: 691,355

[22] Filed: Apr. 25, 1991

[51] Int. Cl.⁵ ............................................. A61B 8/00
[52] U.S. Cl. ..................... 128/660.07; 128/661.08; 128/661.09; 73/861.25
[58] Field of Search ...................... 128/660.07, 660.08, 128/660.09, 661.07, 661.08, 661.09, 661.10; 73/625, 861.25

[56] References Cited

U.S. PATENT DOCUMENTS

| | | | |
|---|---|---|---|
| 3,555,888 | 1/1971 | Brown | 73/67.8 |
| 3,556,079 | 1/1971 | Omizo | 128/662.05 |
| 3,690,311 | 9/1972 | Schorum et al. | 128/660.09 |
| 3,752,255 | 8/1973 | Hill et al. | 73/596 |
| 4,501,277 | 2/1985 | Hongo | 128/660.07 |
| 4,803,990 | 2/1989 | Bonnefous et al. | 128/661.08 |
| 4,932,414 | 6/1990 | Coleman et al. | 128/660.07 |
| 4,937,797 | 6/1990 | Snyder et al. | 128/661.08 |
| 5,038,788 | 8/1991 | Satake | 128/661.09 |

OTHER PUBLICATIONS

Abstract: U.S. Pat. No. 3,777,740, D. Hokanson, Issued Dec. 11, 1973.

Primary Examiner—Francis Jaworski
Assistant Examiner—George Manuel
Attorney, Agent, or Firm—Christensen, O'Connor, Johnson & Kindness

[57] ABSTRACT

A method of position sensing using ultrasound that allows unconstrained motion of a scanhead or sensing probe. Combined with ultrasound echo sensing, a static, B-mode ultrasound imaging system is obtained that does not require mechanical arms or similar structures. The signal acquisition means comprises a scanhead having two or more ultrasound transducers that convert echoes from a subject into echo signals. For B-mode imaging, an image processor processes the echo signals to produce intensity data for a scan line having a known orientation with respect to the scanhead. The echo signals are Doppler processed to produce position data representing the relative positions of a series of scan lines, and a scan converter combines the intensity and position data to produce a two-dimensional image of the subject. The scan converter first processes samples along each scan line to produce intermediate intensity values, and then combines intermediate intensity values for adjacent scan lines to produce the output image.

27 Claims, 8 Drawing Sheets

ULTRASOUND DOPPLER POSITION SENSING

FIELD OF THE INVENTION

The present invention relates to sensing systems in which it is desired to measure the variation of some parameter with position and, in a preferred embodiment, to an ultrasound imaging system in which the sensed parameter is the intensity of backscattered ultrasound energy.

BACKGROUND OF THE INVENTION

In the early days of ultrasound imaging, an ultrasound transducer was mounted on an articulated arm that forced the transducer and the transducer beam to move within a plane. The arm included sensors for measuring the angular position of each of its joints. This angular position data was processed to determine the position of the transducer and the beam direction each time that a one-dimensional echo acquisition was performed. From such measurements, a two-dimensional image of the subject within the plane was assembled. Imaging systems of this type were described as static B-mode scanners.

In the mid-to-late 1970s, static B-mode scanners were gradually replaced by real time ultrasound imaging systems. In a real time system, a scanhead containing the transducer(s) is held essentially stationary, and the ultrasound beam is mechanically or electronically scanned over a series of scan lines in a scanning plane. The scanning is rapid enough so that complete scans through the scanning plane can be made at a rate of 20-30 scans per second, so that a real time, two dimensional moving image can be produced on a display monitor. Real time scanners not only produce moving images, but also avoid the awkwardness of the articulated arm required for static B-mode scanners. In addition, the cost of the mechanical arm and its associated sensors was substantial, approximately the cost of a real time mechanical scanhead, so that static scanners had little price advantage over real time mechanical scanners.

SUMMARY OF THE INVENTION

The present invention provides a sensing system and method in which ultrasound is used to monitor the position of a scanning means, so that variation of the parameter sensed by the scanning means with position can be tracked. In a principal aspect, the invention is applied so as to produce a static, B-mode ultrasound imaging system that does not require mechanical arms or similar structures to track scanhead position.

There are numerous ultrasound applications in which real time imaging is not required, since the subject being imaged is essentially static. There are also many specialty applications of ultrasound, and in particular of medical ultrasound, that are not currently developed to the extent possible, due to the high cost of real time imaging equipment. The ultrasound imaging system of the present invention is capable of serving many of these specialty applications, and of allowing lower cost diagnosis of many medical conditions currently undiagnosed, or diagnosed with expensive, high-end equipment.

The sensing system of the present invention comprises a signal acquisition means that includes scanning means having two or more transducers, and means for causing the scanning means to transmit pulses of ultrasound energy onto a subject, such that echoes backscattered from the subject are received by the scanning means. The scanning means further includes means for converting such echoes into corresponding echo signals for each transducer. The system further comprises sensing means for producing sensor data for the subject for a scan point having a known position with respect to the scanhead. The echo signals are processed by a Doppler processing means, to produce position data representing the relative positions of a series of scan points. The sensor data and position data are then combined to produce an indication of the variation of the sensor data with position.

The ultrasound imaging system of the present invention preferably comprises signal acquisition means, image processing means, Doppler processing means and scan conversion means. The signal acquisition means comprises a scanhead having two or more ultrasound transducers, and means for causing the scanhead to transmit pulses of ultrasound energy into a subject. Echoes backscattered from the subject are received by the signal acquisition means, and converted into echo signals.

The image processing means processes one or more of the echo signals, to produce intensity data for a scan line having a known orientation with respect to the scanhead. The Doppler processing means processes the echo signals to produce position data representing the relative positions of a series of scan lines. The scan conversion means combines the intensity and position data, to produce a two-dimensional image of the subject. Unlike prior mechanical arm static scanners, the present invention derives the scan line position information from the echo signals, an improvement that permits a considerable simplification of the system.

In another aspect, the present invention provides a scan conversion technique, for converting sample values at a plurality of sample points into pixel values at a plurality of pixels. The sample points lie along a plurality of scan lines, and the pixels form an array having two dimensions. For each scan line, the sample values at the sample points lying along the scan line are combined to produce intermediate values for the scan line at a plurality of intermediate points. A first coordinate of each intermediate point is equal to the corresponding coordinate of one of the pixels. Intermediate values of adjacent scan lines are then combined to produce the pixel values.

DETAILED DESCRIPTION OF THE PREFERRED EMBODIMENT

Static Scanning

Figure 1:
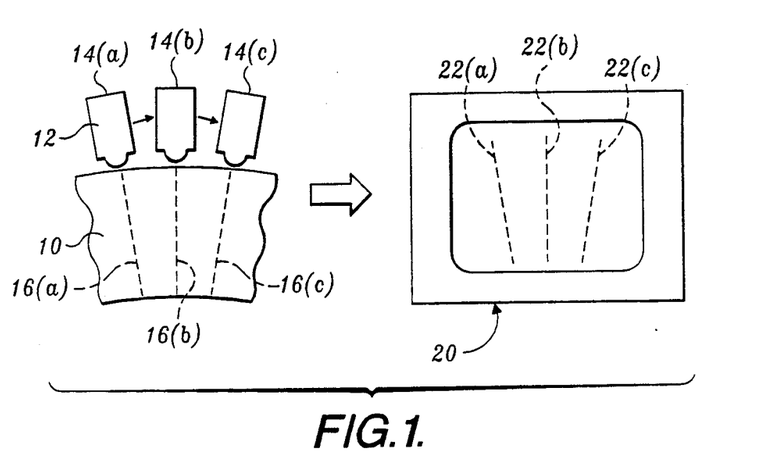
FIG. 1 is a schematic drawing illustrating the static scanning process.

The basic concept of static (as opposed to real time) ultrasound scanning is illustrated in FIG. 1. It is assumed that subject 10 is to be scanned using an ultrasonic imaging system that includes scanhead 12, to create a two-dimensional image of the subject on display unit 20. With the scanhead located at a first position 14(a), one or more pulses of ultrasound energy are transmitted into the subject along scan line 16(a). Some of this ultrasound energy is reflected by discontinuities and other features along the scan line. A portion of the reflected ultrasound energy is received by scanhead 12, and converted into an "echo" signal that represents structures in subject 10 located along scan line 16(a).

Scanhead 12 is subsequently moved to a series of different positions 14(b), 14(c), etc., and the above procedure is repeated at each position. As a result, the ultrasound system receives and stores echo signals for a series of scan lines 16(a), 16(b), 16(c), etc. Knowledge of the relative positions of the scan lines permits reconstruction of a two-dimensional image. In particular, for each scan line 16, the corresponding echo signal is converted into a display line 22 on display unit 20. The relative positioning of display lines 22 on the display unit corresponds to the relative positions of scan lines 16. For the common situation in which the scan line is fixed with respect to the scanhead, the display lines can be positioned from knowledge of the scanhead positions.

Overview of Invention

In prior static scanning systems, the scan line positions have generally been determined from the scanhead positions, the scanhead positions being determined by attaching the scanhead to an articulated arm that included angular position sensor at its joints. In the present invention, the scan line positions are determined from the ultrasound echo signals themselves. In particular, the ultrasound echo signals are analyzed, by a technique commonly referred to as Doppler processing, to determine the velocity of the scan line with respect to the subject during the period of time in which the echo signals are obtained. Integration of this velocity data produces position data that indicates the relative positions of scan lines 16, and therefore of display lines 22.

Figure 2:
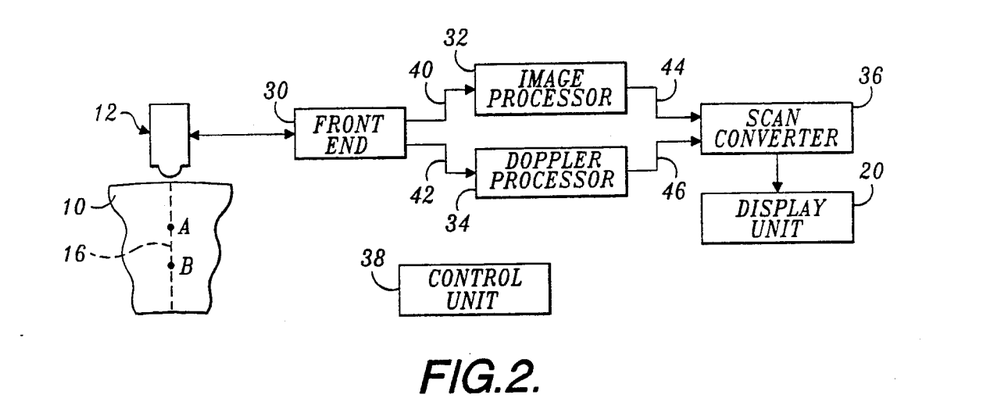
FIG. 2 is a block diagram of a preferred embodiment of an ultrasound imaging system according to the present invention.

A block diagram of a preferred embodiment of the ultrasound imaging system of the present invention is set forth in FIG. 2. The system comprises scanhead 12 and display unit 20, as shown in FIG. 1, as well as front end 30, image processor 32, Doppler processor 34, and scan converter 36. The scanhead and front end are collectively referred to herein as a signal acquisition means. The system also includes control unit 38 that coordinates the operation of the aforementioned components, and that also provides an operator interface.

Front end 30 causes scanhead 12 to emit a series of ultrasonic pulses along scan line 16 that has a known orientation with respect to the scanhead. For example, in a simple solid state scanhead, the orientation of scan line 16 is fixed with respect to the scanhead. The signal acquisition means converts the resulting echoes into echo signals on lines 40 and 42. Image processor 32 processes the echo signals to produce intensity data on line 44, the intensity data representing the intensities of the echoes received along a series of scan lines at different scanhead positions. Doppler processor 34 processes the echo signals from scan lines obtained at multiple scanhead positions to produce position data on line 46 that represents the relative positions of the scanhead and its orientation. Scan converter 36 synthesizes the intensity data and the position data, to generate a display on display unit 20, in the manner generally illustrated in FIG. 1.

In a more complex system, scan line 16 may be mechanically or electronically steered to a series of known orientations with respect to the scanhead between measurements of scanhead position, to produce a plurality of echo image lines at each scanhead position. In this case, scan converter 36 uses the position data and the known orientations of the image lines with respect to the scanhead to determine the relative positions and orientations of the multiple image lines to one another. This permits the generation and display of a complex image that spans a three-dimensional region of the subject, as well as more complex displays that show, for example, multiple 2 D images and their orientation with respect to each other. Such a system could therefore be used to acquire and display three-dimensional ultrasound images.

In a preferred embodiment, the ultrasound system tracks the velocity and position of scanhead 12 by making use of a pair of "range points" A and B that are located at predetermined positions along scan line 16. Using conventional range gating techniques, the Doppler processor utilizes only the echo signals returned from the range points, and ignores the remaining portions of the echo signals. The echo signals from each range point are then analyzed, by techniques described below, to determine the apparent velocity of subject 10 at each range point. The subject, however, is presumed to be stationary, and by reversing the direction of the apparent subject velocity, the velocities of the range points are determined relative to the subject. From the velocities at range points A and B, the translational and rotational velocity of scan line 16 relative to the subject can be determined, by straightforward geometrical transformations. This velocity information is then integrated to determine scan line position and orientation as a function of time.

Imaging and Doppler Modes

It is possible to process each group of echo signals so as to extract both intensity and position data. However, in most ultrasound applications, transmitted pulses that are optimized for image processing are not optimized for Doppler processing, and vice versa. For example, relatively long, narrow bandwidth transmit pulses are usually preferred for Doppler processing, whereas shorter, broader band transmit pulses are usually preferred for imaging. Therefore, in a preferred embodiment of the present invention, the ultrasound system alternates between imaging and Doppler modes, a process that is often referred to as "simultaneous" Doppler operation.

In one representative example of "simultaneous" operation, front end 30 enters imaging mode, and causes scanhead 12 to transmit a single imaging pulse. The resulting echo signal is processed by front end 30 in a conventional manner (e.g., including time gain compensation, beam steering and focusing), and transmitted to image processor 32. The image processor uses the echo signal to produce intensity data on line 44 for a single scan line. The front end then switches to Doppler mode. In Doppler mode, the scanhead transmits a series of Doppler pulses (e.g., eight successive Doppler pulses), and the resulting echo signals are used by Doppler processor 34 to produce position data on line 46. Because the alternation between imaging and Doppler modes occurs at a relatively high rate, e.g., 20 times per second, the slight delay between imaging and Doppler is usually not significant.

Broader Applications

Although the illustrated embodiments of the invention all relate to ultrasound imaging, the present invention has a number of broader applications. In general, the invention provides a technique for tracking the position of a scanning means as the scanning means moves relative to a subject. In an ultrasound imaging system, the scanning means uses ultrasound technology to measure the reflectivity to ultrasound of structures within the subject. However, more broadly, the scanning means could sense any parameter relating to the subject, and the present invention can be used to provide positional information, such that the variation of the sensed parameter with position can be determined.

By way of example, the scanning means could collect one or two-dimensional "color flow" Doppler information from the subject at each scanhead position, to thereby produce data representing one or more two-dimensional color flow images. In such a system, the image processor would comprise a second, "color flow" Doppler processor. The color flow Doppler processor would extract relatively higher frequency Doppler components, to provide conventional color flow information for a scan line or image plane, while the position Doppler processor of the present invention would extract the relatively low frequency components caused by movement of the scanhead.

The invention also has applications outside of the imaging field per se. For example, it may be desired to detect the depth of burn tissue in a burn victim, by using ultrasound to detect the discontinuity at the boundary between the burned and normal tissue. In such a case, it may be preferable to simply determine the depth of the discontinuity as a function of position, without producing or displaying a two-dimensional image. In addition, the parameters sensed by the scanning means may not make use of ultrasound sensing at all. For example, the scanning means could make use of optical, electrical, magnetic, and/or mechanical transducers to measure some parameter of interest, and the present invention would provide the positional information such that the variation of the parameter with position could be determined. By way of example, the invention could be applied to the measurement of the reflectivity, color, roughness, etc. of a surface as a function of position.

Scanhead Configurations

Figure 3:
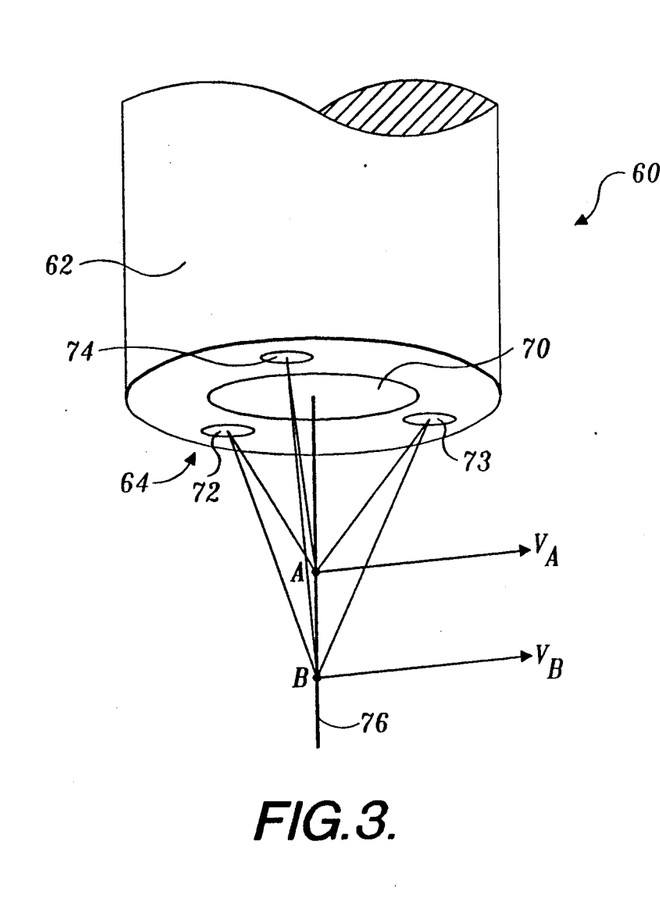
FIG. 3 is a schematic perspective view of a first preferred embodiment of a scanhead.

In one preferred embodiment, the ultrasound imaging system of the present invention utilizes a four element scanhead of the type illustrated by scanhead 60 in FIG. 3. Scanhead 60 comprises a generally cylindrical body 62 having a face 64 that includes central transducer 70, and three smaller outer transducers 72-74 positioned symmetrically about the central transducer. In imaging mode, ultrasound pulses are transmitted and received only on central transducer 70, to thereby produce an echo signal for a scan line 76 that is normal to face 64, and centrally located with respect to central transducer 70.

In Doppler mode, pulses are transmitted by central transducer 70, and received by all four transducers. Outer transducers 72-74 are made small enough, compared to the ultrasound wavelength, so that their sensitivity regions overlap at range points A and B along scan line 76. Physical aiming of the outer transducers, and/or focusing, can also be used to improve their sensitivity at the range points. Thus in Doppler mode, the ultrasound system produces echo signals for each of range points A and B, for each of transducers 70 and 72-74. These echo signals are processed, as further described below, to determine the three dimensional velocities $V_A$ and $V_B$ of the range points A and B with respect to the subject.

The velocities $V_A$ and $V_B$ are measured at time intervals of $\Delta t$, i.e., each time the system enters Doppler mode. For each velocity measurement, the displacement of each range point in three dimensions can be predicted by multiplying each velocity component by $\Delta t$. For a short enough time interval, this amounts to numerical integration of the velocity components, to obtain the three dimensional position of each range point as a function of time. Since the range points are fixed relative to the scan line, the positions of the range points allow the scan line position and orientation to be calculated. Furthermore, for the following discussion, it will be assumed that the scan line has a fixed position with respect to the scanhead. Thus, the scan line position and orientation and the scanhead position and orientation will be used interchangeably.

The three-dimensional velocity V at only one range point would be sufficient to determine simple translation of the scanhead. However, the velocity and position of two range points are preferably computed, to make it possible to determine motions such as rotation of the scanhead about one range point. To detect rotation of the scanhead around scan line 76, a third, non-colinear range point would be required. However, this motion is rarely significant in terms of image formation, and may therefore generally be ignored.

Figure 4:
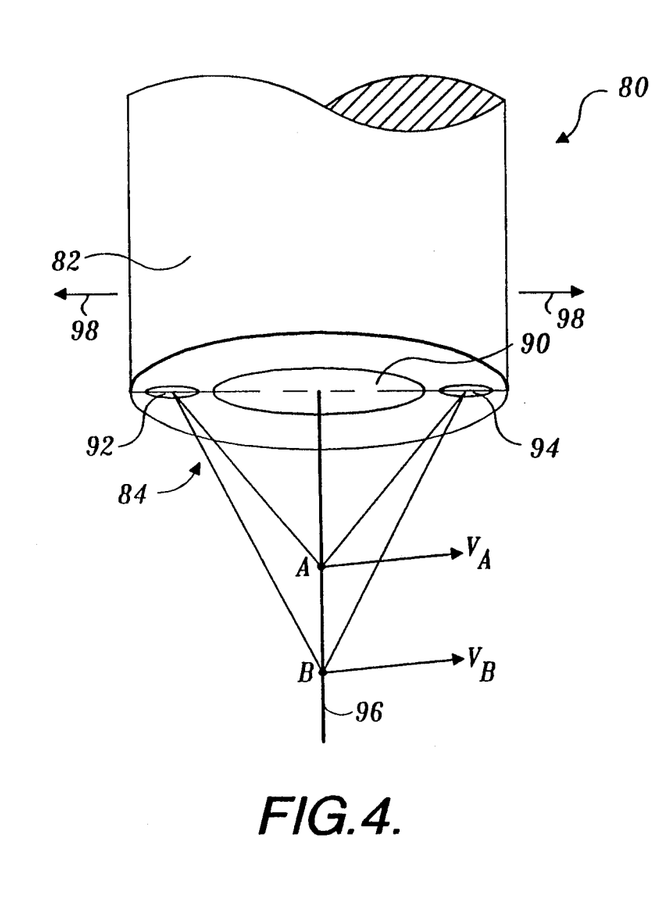
FIG. 4 is a schematic perspective view of a second preferred embodiment of a scanhead.

In a second preferred embodiment, the ultrasound imaging system of the present invention utilizes a three transducer scanhead of the type illustrated in FIG. 4. Scanhead 80 comprises cylindrical body 82 having face 84. Face 84 includes central transducer 90 and outer transducers 92 and 94 that are positioned on opposite sides of central transducer 90 from one another. As with the previously described embodiment, in imaging mode, ultrasound pulses are transmitted and received only on the central transducer 90, to thereby produce an image signal for scan line 96 that is normal to face 84, and that is centrally located with respect to central transducer 90.

In Doppler mode, pulses are transmitted by central transducer 90, and received by all three transducers. As in the prior embodiment, the outer transducers may be aimed and/or focused, so that their sensitivity regions overlap at range points A and B that are located along scan line 96. For each range point, the echo signals produced by the front end are processed to determine the range point velocities $V_A$ and $V_B$ in a two-dimensional scanning plane that contains scan line 96, and that passes through the centers of all three transducers. Movement out of the scanning plane cannot be detected. Thus a user of scanhead 80 must attempt to move the scanhead in the scanning plane. Body 82 preferably includes suitable markings and/or tactile features to enable a user to identify the desired scanning plane.

Figure 5:
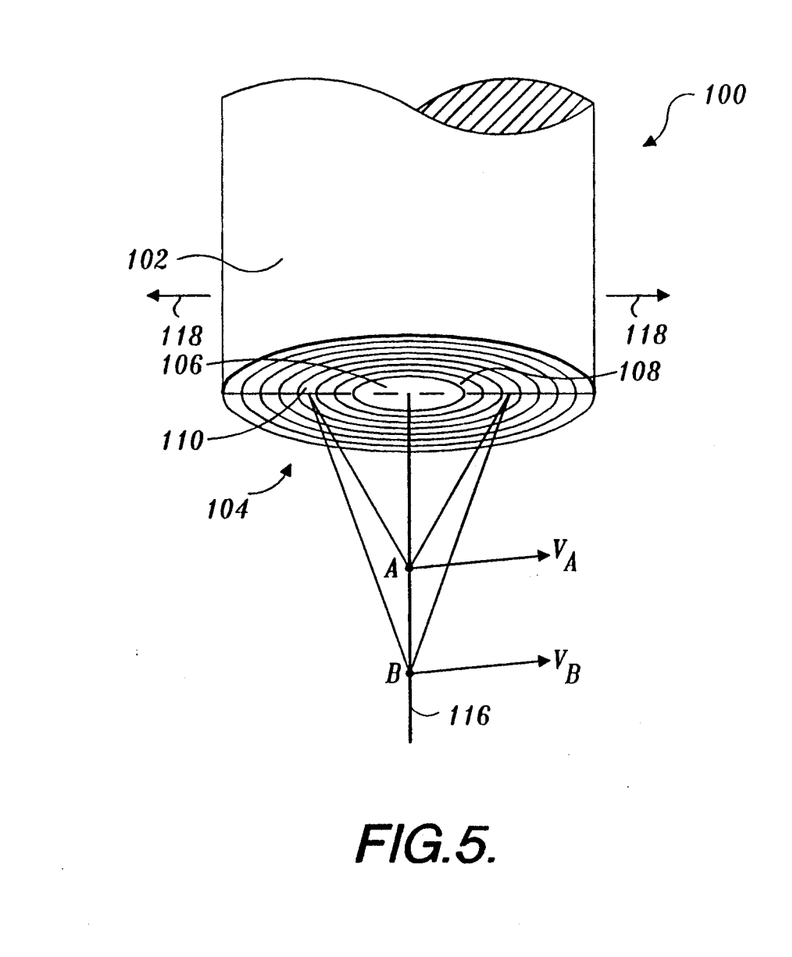
FIG. 5 is a schematic perspective view of a third preferred embodiment of a scanhead.

FIG. 5 illustrates a third preferred embodiment for a scanhead for use in the present invention. The illustrated scanhead 100 includes a cylindrical body 102 having face 104. Face 104 includes a central transducer 106 and a series of concentric ring-shaped transducers 108 disposed around the central transducer at different radii. The illustrated transducer is an example of an annular array transducer of the kind well known in the medical ultrasound arts. For this embodiment, in imaging mode, all transducers are used in a conventional manner. In Doppler mode, central transducer 106 and a selected annular transducer 110 are used to provide the echo signals.

For the transducer of FIG. 5, the assumption is made that the operator moves the scanhead in a scanning plane defined by scan line 116 and scanning direction 118. In a method similar to that described in the embodiments of FIGS. 3 and 4, central transducer 106 is used to transmit, and central transducer 106 and annular transducer 110 are used to receive. However, unlike the prior embodiments, annular transducer 110 receives echo signals from a range of angles with respect to the velocity vectors $V_A$ and $V_B$ of the range points, thereby giving rise to a range of Doppler shift frequencies. However, if the velocity vector $V_A$ is always confined to a single plane, the minimum Doppler angle with respect to the velocity vector will always be found at one edge of the annular transducer. This edge will coincide with the intersection of the scanning plane with the annular transducer. Since a smaller Doppler angle gives rise to a larger Doppler effect, this portion of the annular transducer will therefore receive the greatest Doppler shift frequency. This point is discussed again below, in connection with specific techniques for extracting velocity and position information from the echo signals.

Doppler Processor

The term "Doppler effect" describes the phenomena that when a source of sound is in motion, the motion modifies the pitch of the sound, as measured by a stationary observer. For motion towards the observer, the pitch is increased; for motion away, the pitch is decreased. This change in frequency $\Delta f$ is governed by the following equation:

$$\Delta f = f_0(v/c) \cos \theta \tag{1}$$

where $f_0$ is the frequency of the sound emitted by the source, v is the velocity of the source, c is the speed of sound in the propagation medium between the source and the observer, and $\theta$ is the angle between the source's motion vector and the line of sight to the observer.

For ultrasound imaging of moving structures in a subject, the situation is somewhat different. First of all, for pulsed Doppler sensing, short bursts of sound energy are transmitted into the body from a stationary transducer and reflected by moving objects. This results in a factor of 2 increase in the frequency shift detected back at the transducer. Secondly, the frequency shift imparted to each pulse as it reflects from a moving object is not the quantity measured by the ultrasound system. Instead, the phase difference between successive pulses as they return to the transducer is tracked, and the rate of change of this phase is the quantity associated with the Doppler shift frequency. This approach is necessary due to the frequency dependent attenuation of most subjects (e.g., the human body), which distorts ultrasound pulses as they travel, making it virtually impossible to accurately measure a frequency shift on the pulse directly. Therefore, the Doppler shift effect for ultrasound is in reality an echo shift in time caused by displacement of the moving object. Since the formula for the frequency shift produced by the rate of change of phase is exactly the same as the frequency shift specified by the Doppler equation, the ultrasound method of motion detection is commonly referred to as Doppler sensing.

For the case in which an ultrasound pulse is emitted from a stationary source and reflected by a scatterer moving at velocity v, the rate of change of phase $\Delta f$ measured at the source is given by:

$$\Delta f = 2f_0(v/c) \cos \theta \tag{2}$$

where $\theta$ is the angle between the source to scatterer line and the velocity vector of the particle. It can be seen that Equation 2 is identical to Equation 1, except for the factor 2. For the case in which the transmitter and receiver are located at different positions, equation 2 becomes:

$$\Delta f = f_0(v/c)(\cos \alpha + \cos \beta) \tag{3}$$

where $\alpha$ is the angle between the transmitter-scatterer line and the scatterer's velocity vector, and $\beta$ is the angle between the scatterer-receiver line and the velocity vector. It can be seen that Equation 3 reduces to Equation 2 for the case in which $\alpha$ equals $\beta$.

Figure 6:
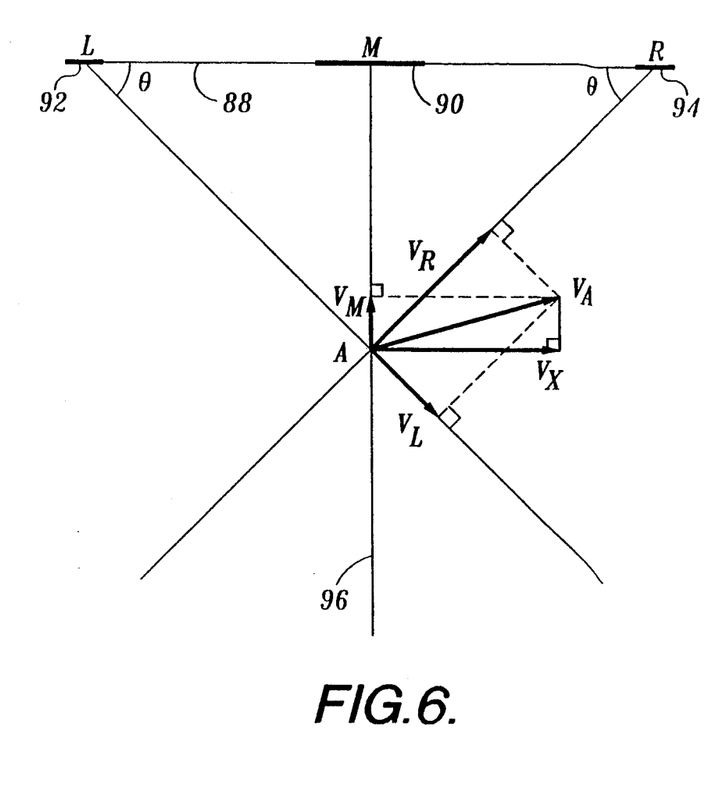
FIG. 6 is a graph illustrating the calculation of velocity at a range point.

FIG. 6 is a diagram showing how Equations 1-3 above may be applied to the scanhead geometry shown in FIG. 4, to permit calculation of the velocity vector $V_A$ for range point A from the measured Doppler shifts at transducers 90, 92 and 94. In FIG. 6, central transducer 90 is labeled M (for middle), and peripheral transducers 92 and 94 are labeled L (left) and R (right), respectively. Doppler pulses are transmitted by transducer M, and received on all three transducers. Vectors $V_M$, $V_R$, and $V_L$ represent the projections of $V_A$ onto the lines connecting range point A to the respective transducers.

The Y axis will be taken to be coincident with scan line 96, and the X axis will be taken to be coincident with line 88 joining the three transducers. Thus the X axis lies in the scanning direction, and the X and Y axes define the scanning plane. Using Equations 1-3, it can be shown that the projections fo vector $V_A$ into this X-Y coordinate system are:

$$V_y = V_M = \frac{c}{2f_0} \Delta f_{MA} \tag{4}$$

$$V_x = \frac{(\Delta f_{RA} - \Delta f_{LA})c}{2f_0 \cos\theta} \tag{5}$$

The quantities $\Delta f_{MA}$, $\Delta f_{RA}$, and $\Delta f_{LA}$ are the Doppler shifts measured at transducers M, R, and L, respectively, and $\theta$ is the angle between the X axis and the line joining range point A to transducers L and R, as shown in FIG. 6.

The components $V_X$ and $V_Y$ are actually the velocity of the subject with respect to range point A. The velocity of range point A with respect to the subject is found by taking the negative of these values. Thus if we designate the orthogonal velocity components of range point A with respect to the subject as $A_X$ and $A_Y$, these components are given by:

$$A_x = \frac{(\Delta f_{LA} - \Delta f_{RA})c}{2f_0 \cos\theta} \tag{6}$$

$$A_y = \frac{-\Delta f_{MA} c}{2f_0} \tag{7}$$

Identical equations may be used to relate the frequency shifts measured at range point B ($\Delta f_{LB}$, $\Delta f_{RB}$, and $\Delta f_{MB}$) to velocity components $B_X$ and $B_Y$.

The velocity components set forth in Equations 6 and 7, and the corresponding equations for range point B, can be used to calculate the displacement and rotation of scan line 96 for a time interval $\Delta t$. In particular, if $\Delta x$ and $\Delta y$ represent the translational motion of central transducer 90, and if $\Delta \Phi$ represents the rotation of scan line 96, then the appropriate relationships are as follows:

$$\Delta X = [A_x + R(A_x - B_x)]\Delta t \cos\Phi - [A_y + R(A_y - B_y)]\Delta t \sin\Phi \tag{8}$$

$$\Delta Y = [A_x + R(A_x - B_x)]\Delta t \sin\Phi + [A_y + R(A_y - B_y)]\Delta t \cos\Phi \tag{9'}$$

$$\Delta\Phi = \sin^{-1}\left[\frac{\Delta t(A_x - B_x)}{R_B - R_A}\right] \tag{10}$$

In equations 8–10, $R_A$ and $R_B$ represent the distances from transducer M to range points A and B respectively, R is equal to $R_A/(R_B - R_A)$, and $\Phi$ represents the orientation of scan line 96 with respect to a fixed X-Y coordinate system.

For scanheads of the type shown in FIG. 4, Equations 6–10 are used by the Doppler processor to produce two-dimensional position data based upon the Doppler frequency shifts measured at each of the three transducers, and at each of the two range points. For scanheads of the type shown in FIG. 3, similar equations may be derived for producing three dimensional position data based upon the Doppler shifts measured at four transducers. It will be apparent that numerous other scanhead configurations may also be used. For example, referring to FIG. 6 and Equations 4 and 5, it will be seen that the velocity component $V_y$ could be derived from $\Delta f_{RA}$ and $\Delta f_{LA}$, rather than from $\Delta f_{MA}$. Thus, the present invention could utilize a scanhead having only two tranducers, to detect movement of the scanhead within a scanning plane. However, the three-transducer embodiment illustrated in FIGS. 4 and 6 will in most cases provide higher accuracy.

For an annular array type scanhead, such as the one shown in FIG. 5, an extra step is generally required to produce the position data. As previously described, for annular transducer 110 of scanhead 100, the peak frequency shift is assumed to come from the edge of the annular transducer in the plane of the scan. Thus if the direction of scanhead motion is roughly perpendicular to scan line 116, the peak frequency Doppler shift will be approximately the same from both edges of the annular transducer that intersect the scanning plan. If the direction of motion is not perpendicular to scan line 116, one edge will have a larger Doppler frequency shift than the other, due to the fact that the Doppler angle for that edge is smaller.

Figure 7:
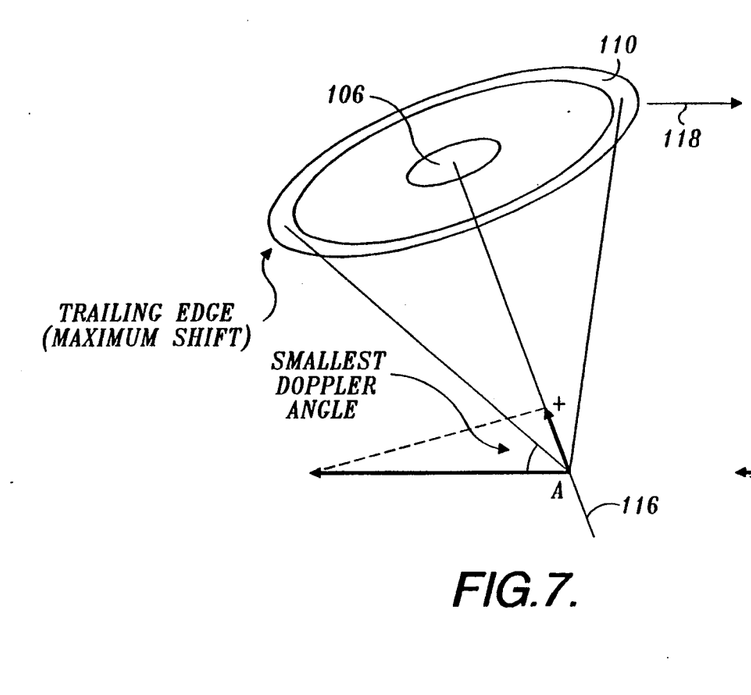
FIG. 7 is a schematic view illustrating an annular array transducer receiving a positive Doppler shift signal.
Figure 8:
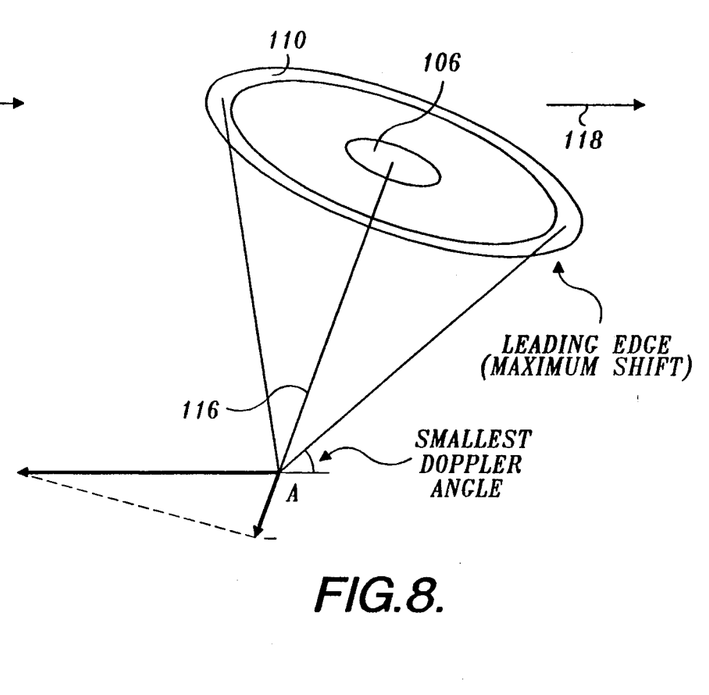
FIG. 8 is a schematic view illustrating an annular array transducer receiving a negative Doppler shift signal.

The edge having the larger shift can be found by examining the sign of the Doppler shift frequency detected by the central transducer 106. If the sign is positive, the subject at the range point has a velocity component towards the scanhead, and the maximum frequency shift will be received by the trailing edge of annular transducer 110 with respect to the scanhead motion. This situation is illustrated in FIG. 7. On the other hand, if the sign is negative as in FIG. 8, the velocity is away from the scanhead, and the maximum frequency shift will be detected by the leading edge of annular transducer 110, as shown in FIG. 8. With knowledge of which edge of the annular transducer is receiving the maximum Doppler shift, along with a detected Doppler shift along scan line 116, two linearly independent vector components can be computed, to determine the two-dimensional velocity vector in the scanning plane. This computation is performed for each of the range points A and B, as previously described. Equations 6–10 are then applied as in the embodiment of FIG. 4.

The advantage of the FIG. 5 approach is that it allows the use of a standard scanhead geometry, namely an annular array, for both imaging and position sensing. For the annular array approach, it may be advantageous to use estimates of the Doppler spectrum other than peak frequency, such as spectral width or variance, to compute velocity of the range points.

Microcomputer Embodiment

With the low cost Doppler position sensing provided by the present invention, together with low scanhead costs made possible by a static design (no moving parts) and simple geometry, the cost of an ultrasound imaging system can be significantly reduced. The remaining system cost is mostly associated with the processing electronics, the display subsystem, and the user interface. The rapid evolution of microcomputers in recent years, both in terms of increased performance at lower cost, and better image display capability, now provides a low cost means of implementing these remaining functions. In particular, the modern personal computer can be used as a platform for a static B-scan system, providing facilities for housing electronic circuit boards, an operator interface, a software operating system, and means for processing signals and displaying images.

Figure 9:
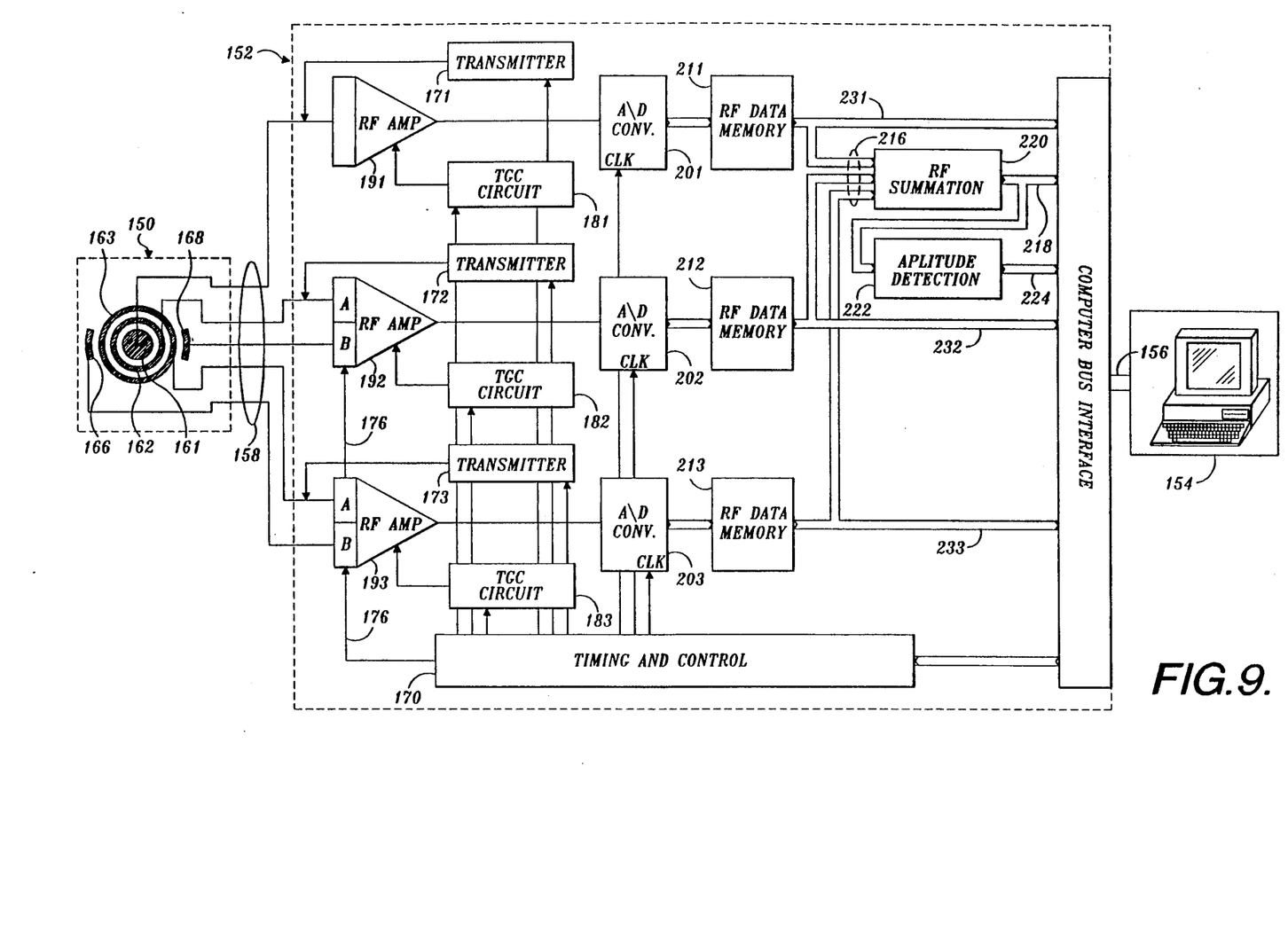
FIG. 9 is a block diagram of a preferred embodiment of the signal acquisition module.

A preferred embodiment of a low cost, PC-based ultrasound scanning system according to the present invention is schematically illustrated in FIG. 9. The scanning system comprises scanhead 150, acquisition module 152 and microcomputer 154. Acquisition module 152 is coupled to the microcomputer bus 156 and, in a preferred arrangement, comprises one or more boards that plug directly into expansion slots of the microcomputer. The board preferably includes an externally accessible connector through which scanhead 150 is connected to the acquisition module via cable 158.

In the embodiment of FIG. 9, scanhead 150 comprises central transducer element 161, annular transducers 162 and 163 disposed concentrically about the central transducer, and outer transducers 166 and 168 positioned symmetrically on opposite sides of the central and annular transducers. A scanhead of this type may be formed from a conventional annular array transducer having a central element and three rings, by modifying the outermost ring to form outer transducers 166 and 168. In operation, transducers 161-163 are used for imaging in a manner conventional for annular array transducers. Such arrays produce narrow beam patterns for high resolution imaging. Transducers 161, 166 and 168 are used for Doppler processing in a manner similar to that described above in connection with FIG. 4.

Acquisition module 152 includes timing and control circuit 170, transmitters 171-173, TGC (time gain control) circuits 181-183, and RF amplifiers 191-193. Transmitters 171-173 are coupled to transducers 161-163 respectively. In imaging mode, all three transmitters are used in a conventional manner for annular array transducers. In Doppler mode, only central transducer 161 is energized by transmitter 171.

RF amplifier 191 has a single input that is coupled to central transducer 161. RF amplifier 192 has A and B inputs, the A input being coupled to annular transducer 162, and the B input being coupled to outer transducer 168. RF amplifier 193 also has A and B inputs, the A input being connected to annular transducer 163, and the B input being coupled to outer transducer 166. In imaging mode, selection signals received from timing and control circuit 170 via lines 176 cause selection of the A inputs, such that RF amplifiers 191-193 receive echo signals from transducers 161-163 respectively. During Doppler mode, the B inputs of RF amplifiers 192 and 193 are selected, such that RF amplifiers 191-193 receive echo signals from transducers 161, 168 and 166 respectively. For each RF amplifier, the gain is dynamically controlled by the corresponding TGC circuit in a conventional manner.

Acquisition module 152 also includes A/D converters 201-203, RF data memories 211-213, RF summation circuit 220, and amplitude detection circuit 222. A/D converters 201-203 receive the amplified echo signals from RF amplifiers 191-193 respectively, and convert the echo signals into digital samples that are stored in RF data memories 211-213 respectively. Data stored in the RF data memories in imaging mode is read out of these memories with the appropriate variable signal delays to provide focusing, via buses 216 into RF summation circuit 220. The summation circuit outputs the resulting digital summation signal on bus 218. The summed image data may be made directly available on bus 156, or may be further processed by amplitude detection circuit 222 that essentially performs envelope detection on the summed signal. The amplitude detection circuit produces image data that is placed directly on microcomputer bus 156 via bus 224. Although the RF summation and amplitude detection functions could be performed by the microcomputer in software, the illustrated hardware implementation is preferred, given current microcomputer processing speeds.

Data stored in RF data memories 211-213 in Doppler mode is read out directly to microcomputer bus 156 via data buses 231-233 respectively. For simplicity, Doppler echo data corresponding to a complete scan line is stored in the RF data memories 211-213. However, only data corresponding to range points A and B is required, and hence only a subset of the stored data needs to be read out and processed by microcomputer 154.

Data processing functions performed by microcomputer 154 include the processing of the Doppler data to determine the position of each display line, followed by a combination of the image data produced by amplitude detection circuit 222 with such position information, to produce a display. Thus the microcomputer performs the functions of Doppler processor 34 and scan converter 36 shown in FIG. 2. Preferably, microcomputer 154 can access the data stored in RF data memories 211-213 in the same manner that it accesses its own system memory.

Acquisition module 152 receives its control instructions from the microcomputer operating system, performing its tasks as requested by the operator through a software program which provides an interface to the user. This software provides the means for initiating and halting a scanning sequence, adjusting system parameters such as imaging depth, transducer power output and system gain. Subprograms can also be provided which allow the operator to make measurements on the images collected, and allow for archival storage and retrieval to various forms of digital storage media. These are routine functions for nearly all modern ultrasound imaging systems, and are well within the ability of those skilled in the art. The standard computing environment makes implementation of many of these ancillary software programs much easier than if implemented in a custom system design.

In contrast to the conventional software functions described above, the scan conversion performed by microcomputer 154 is not conventional for at least two reasons. First, scan conversion on present day ultrasound imaging systems is performed by a combination of software and dedicated hardware. In the embodiment of FIG. 9, the scan conversion is done in software. Second, most scan conversion techniques assume that the scan lines are equally spaced from one another in angle, as a consequence of the mechanical or electronic scanning performed by the instrument. By contrast, in the present invention, the spacing of scan lines is in general unpredictable, because it is based upon the speed at which the operator moves the scanhead.

A preferred scan conversion technique for the system of the present invention is outlined in FIGS. 10-13. To make the discussion more concrete, it will be assumed that the output of the scan conversion will be a raster image having 640 horizontal pixels and 480 vertical pixels, as diagrammed in FIG. 10. The horizontal and vertical pixel spacings are equal, and each pixel will be encoded by an 8-bit gray level value. The task of the scan converter is to take the intensity data for each scan line, such as scan lines 260 and 262 shown in FIG. 10, and write such intensity values to the appropriate pixels on the raster image, using the most recent Doppler position data.

Figure 11A:
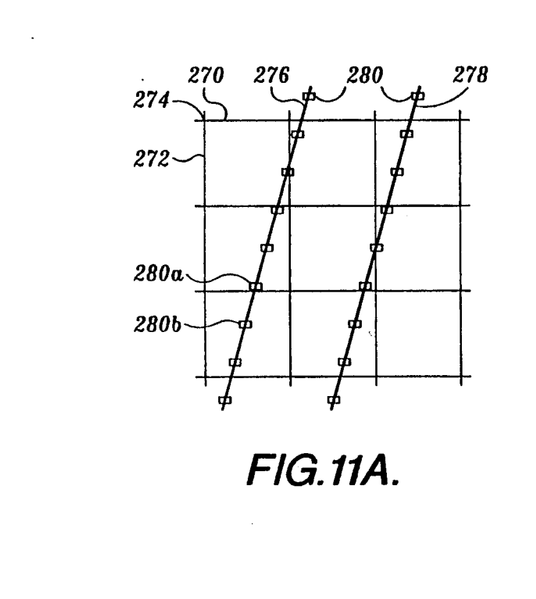
FIGS. 11A-11C are graphs illustrating a preferred embodiment of the scan conversion process.
Figure 11B:
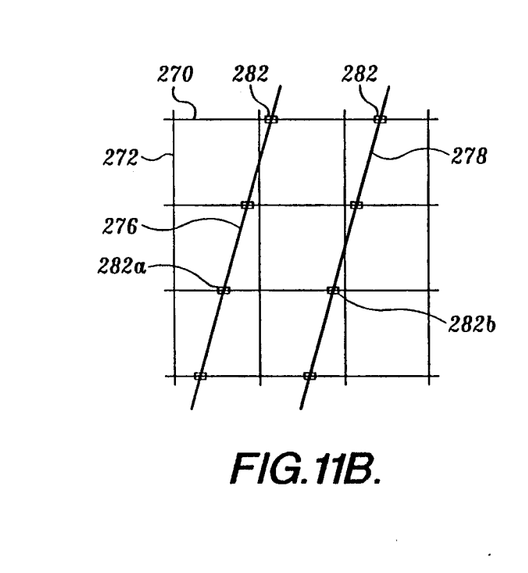
Figure 11C:
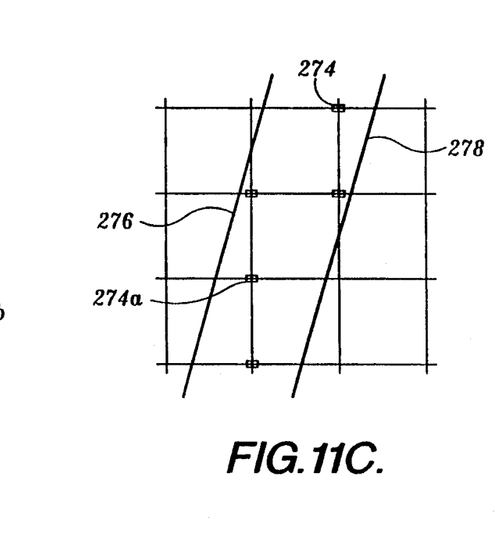

Referring now to FIGS. 11A-11C, each of these figures shows a portion of the raster display to be generated. This portion includes a plurality of evenly spaced horizontal raster "lines" 270, and a plurality of evenly spaced vertical raster "columns" 272. Each intersection of a line 270 and a column 272 represents a pixel 274 in the display. The raster portions shown in FIGS. 11A-11C are traversed by two scan lines 276 and 278. The intensity data produced by the acquisition module represents the echo intensity at a plurality of sample points 280 along each scan line, the sample points in general being evenly spaced along the scan line. Thus the input to the scan conversion process comprises intensity data at sample points 280, while the desired output of the scan conversion process is intensity data at each pixel 274.

In a preferred embodiment, the scan conversion comprises two principal steps. In the first step, the intensity values at sample points 280 along each scan line are combined to produce intensity values for intermediate points 282 shown in FIG. 11B. In the second step, the intensity values at intermediate points 282 are combined to produce intensity values at pixels 274 (FIG. 11C).

For the first combining step, the locations of intermediate points 282 are preferably selected based upon the orientation of each individual scan line (276, 278). In particular, the intermediate points for a given scan line are the intersection of that scan line with either lines 270 or columns 272, the choice between lines and columns being made so as to maximize the number of intermediate points generated for each scan line. Thus in FIG. 11B, scan line 276 is more nearly parallel to columns 272 than to rows 270, and thus each intermediate point 282 for scan line 276 is located at the intersection of scan line 276 with one of the rows 270. The same is true for scan line 278. However for scan line 262 of FIG. 10, for example, the first combining step would use intermediate points positioned at the intersections of the scan line and the display columns.

The intensity value for each intermediate point 282 is preferably determined from the intensity values at the two sample points 280 located on opposite sides of the intermediate point along the display dimension to which the scan line is most nearly parallel. For example, the intensity value for intermediate point 282a (FIG. 11B) may be determined from linear interpolation of the intensity values at sample points 280a and 280b (FIG. 11A). Other types of interpolation or estimation could also be used. However, preferably, only the sample points lying along a given scan line are used to produce data for the intermediate points along that scan line. Thus the first combining step occurs on a scan line-by-scan line basis.

In the second combining step, the intensity values at intermediate points 282 are used to calculate intensity values for pixels 274 (FIG. 11C). Preferably, the intensity value for each pixel is determined from the intensity values at the two intermediate points located on opposite sides of the pixel along the display dimension to which the scan line is most perpendicular. For example, the intensity value for pixel 274a in FIG. 11C may be determined by linear interpolation between the intensity values at intermediate points 282a and 282b in FIG. 11B.

Figure 12:
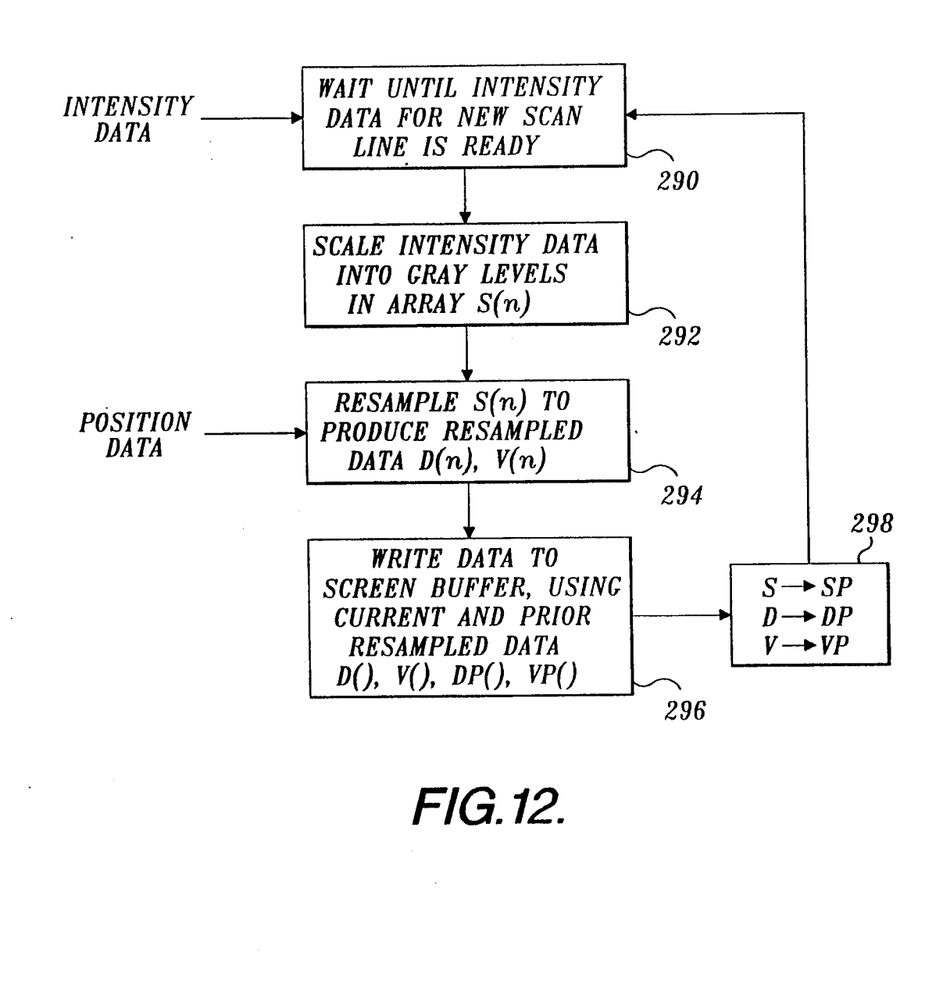
FIG. 12 is a flow chart for a preferred embodiment of the scan conversion process.

An outline of a preferred embodiment of the scan conversion process carried out by microcomputer 154 is shown in FIG. 12. In block 290, the software waits for the intensity data for a new scan line to become available. The availability of new intensity data will typically be indicated by a signal received from the acquisition module. Software block 292 then scales the intensity data into a suitable gray scale, e.g., an 8-bit, 256 level gray scale, and places the scaled data into sample array S(n), where n may typically range from 0 to 1024.

In block 294, the software combines the sample data S( ), based upon the current position data, to produce resampled arrays D( ) and V( ). The resampling is carried out in one of two different ways, depending upon the current value of $\phi$, $\phi$ being the angle between a given scan line and downward direction of the vertical display axis. For the case in which the absolute value of $\phi$ is less than or equal to 45°, as exemplified by scan line 260 in FIG. 10, the array D( ) designates horizontal position in pixel units (i.e., each value of D lies in the range 0-639), the array V( ) designates the resampled intensity, and the array index specifies the vertical screen coordinate (in pixels or "horizontal raster lines"). If no intensity value can be calculated for a given horizontal raster line N, then the values D(N) and V(N) are set to zero. Thus, for example, for scan line 260, the D( ) and V( ) values for subscripts less than 80 and greater than 340 are set to zero.

Figure 10:
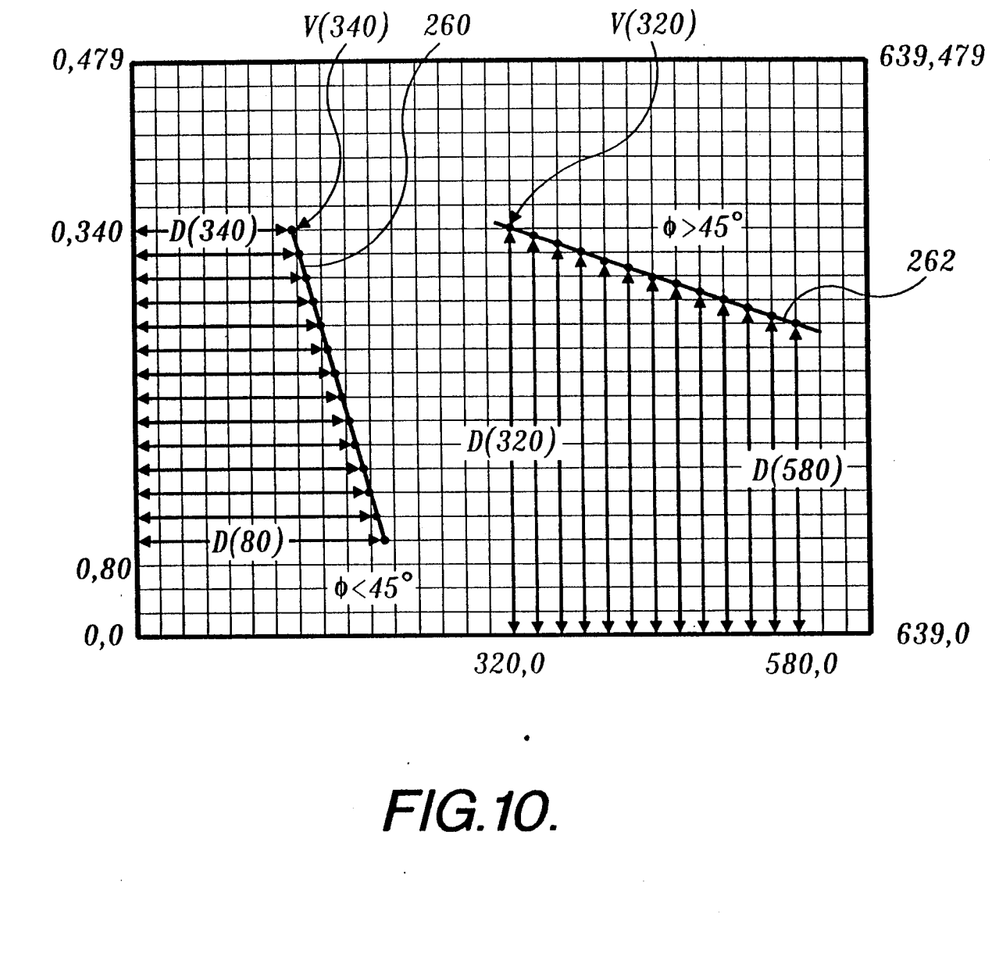
FIG. 10 is a graph illustrating the mapping of display lines to a raster display.

For the case in which the absolute value of $\Phi$ is greater than 45° but less than 135°, as exemplified by scan line 262, array D specifies vertical position (in pixel units or vertical raster lines), array V specifies resampled intensity, and the subscript specifies horizontal position in pixels. If no sample point is found for a given vertical raster line, the corresponding D( ) and V( ) values are set to zero. Finally, for the case in which the absolute value of $\Phi$ exceeds 135°, the processing is the same as for the case when the absolute value of $\Phi$ is less than or equal to 45°.

Figure 13:
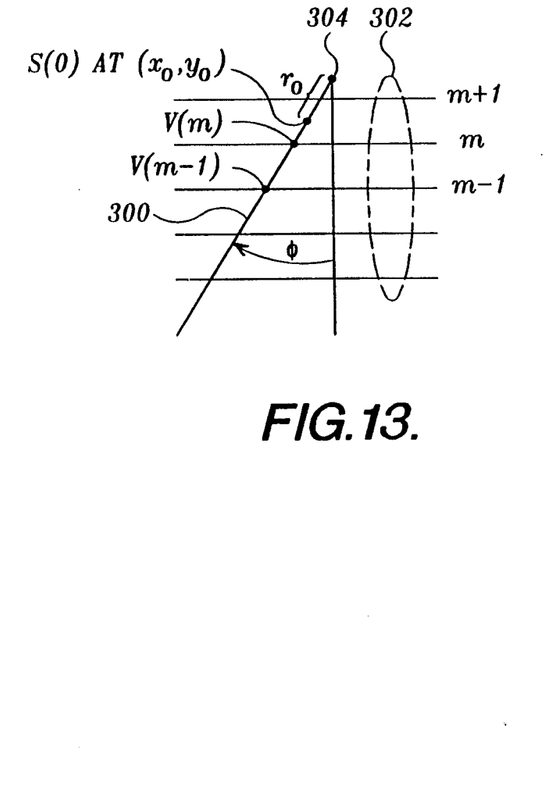
FIG. 13 is a diagram illustrating the resampling process.

The process of producing the D( ) and V( ) array is illustrated in FIG. 13, for a scan line 300 having a negative value of $\phi < 45°$ and where $|\phi| < 45°$. It is desired to resample the data S( ) along scan line 300 to produce data at intermediate points located at the intersection of scan line 300 with each of horizontal raster lines 302. The process begins by calculating the position of the first sample point S(0) in pixel units $(x_o, y_o)$, using the known position (x, y) of the origin 304 of the beam and the range distance to the first sample point. If the range distance is $r_o$ (in pixels), then $$x_o = x + r_o \sin \phi \qquad (11)$$

$$y_o = y - r_o \cos \phi \qquad (12)$$

The position $(x_o, y_o)$ of S(0) will serve as a reference point for the calculation of new samples points. Next calculate $s_r$, the number of samples in S( ) (with fractional part) between adjacent pixel rows. Since the samples points in S(n) are spaced equally in time, they are also spaced equally in distance, and the increment of distance, $d_p$, can be expressed in pixel units for a given scale factor of distance to pixel units. This constant value of $d_p$ can then be used to compute $s_r$ by the following formula.

$$s_r = (1/d_p)/\cos \phi \qquad (13)$$

The first non-zero value of V(n) is then calculated for the raster line m, where m is found by taking the integer value of $y_o$. The value of V(m) is calculated by first multiplying the fractional value of $y_o$ times $s_r$ to obtain a sample number, $n_m$. The sample number's integer and fractional parts are then used to perform a bilinear interpolation between adjacent actual samples of S(n).

$$n_m = s_r \text{frac}(y_o) \quad (14)$$

If we let $n = \text{int}(n_m)$ and $f = \text{frac}(n_m)$, then $$V(m) = (1-f) S(n) + f S(n+1) \quad (15)$$

The displacement value (distance along horizontal raster from left edge to point V(m) in pixel units) for D(m) is found from the position of the first sample $(x_o, y_o)$ by the formula $$D(m) = x_o + \text{frac}(y_o) \tan \phi \quad (16)$$

Successive values of V(n) for each raster line are found by accumulating the value $s_r$ for each decrease in the raster line number, and then adding $n_m$. This gives a new sample number $n_s$ which can be used to index into S(n). For raster line $m-i$, where i ranges from 0 to m, we have $$n_s = n_m + i s_r \quad (17)$$

Letting $n = \text{int}(n_s)$ and $f = \text{frac}(n_s)$, we can again apply equation (15) to obtain the value of $V(m-i)$.

$$V(m-i) = (1-f)S(n) + f S(n+1) \quad (18)$$

The accompanying values of $D(m-i)$ are found by accumulating $\tan \phi$ and adding to D(m) for each new raster line.

$$D(m-i) = D(m) + i \tan \phi \quad (19)$$

Equations 18 and 19 are applied for successive values of i until $i = m$, or until the range of samples in S(n) is exceeded. An entirely analogous technique is used for the case in which $\Phi$ exceeds 45°.

Returning again to FIG. 12, once the current intensity data S() has been resampled, the next step, in block 296, is to utilize the newly computed D() and V() arrays to write the new intensity data to the screen buffer. This is preferably done using the newly resampled data D() and V(), together with the corresponding data for the prior scan line, DP() and VP(). The buffers D(n), V(n) and S(n) are then written to DP(n), VP(n) and SP(n) respectively (block 298), and D(n), V(n) and S(n) are cleared.

In block 296, the new buffers D(n) and V(n) are compared with the previous buffers DP(n) and VP(n) for each n, and actions to write pixels in the raster display are taken depending on the outcome of the comparison. If for some value of n the new and previous data are closest to the same pixel, the values of V(n) and VP(n) are combined by some formula, and the result replaces the old pixel value. If the current and previous data for some value of n are closest to different pixels, then intermediate pixels are also written by interpolation of VP(n) and V(n). The following steps detail this process, and are taken for n=0 to 479:
1. If D(n)=0, go to 9.
2. If D(n) is not equal to 0 and V(n)=VP(n)=0, go to 9.
3. If DP(n)=0, then go to 8.
4. Let j=rounded value of DP(n) and k=rounded value of D(n); If j=k, then use a designated formula to combine V(n) and VP(n) into new value, and write back into V(n); go to 8.
5. If $|k-j|=1$, go to 8.
6. If DP(n) less than D(n), then for x=j to k in integer steps, compute and write pixel values by linear interpolation over distance d=D(n)−DP(n). Go to 9.
7. If D(n) less than DP(n), then for x=k to j in integer steps, compute and write pixel values by linear interpolation over distance d=DP(n)−D(n). Go to 9.
8. Round D(n) to get x pixel address; use n for y pixel address; write value V(n) to (x,y).
9. Increment n; if n less than 480, go to 1, else done.

A suitable formula for combining V(n) and VP(n) when the same pixel is addressed is $\frac{1}{2}$ [V(n)−VP(n)]. This performs a type of averaging which will reduce noise in the image. Another technique is to take the maximum value of V(n) and VP(n). This type of processing increases the detectability of low level echoes, and reduces effects of specularity of echo targets.

When the value of $|\phi|$ first becomes greater than 45°, an extra processing step is taken. The buffers D(n) and V(n) are computed in the same manner as above, and the new pixels are written to the raster. However, instead of copying D(n) and V(n) to DP(n) and VP(n), DP(n) and VP(n) are computed from S(n) with DP(n) now representing the vertical distance in pixels from the bottom of the raster plane for each column of pixels in the image. The process is very similar to that described above, with the exception that the horizontal and vertical directions are exchanged. Thereafter, for each new data structure with $45° < |\phi| < 135°$, D(n) and V(n) are calculated in the same manner, with D(n) representing the vertical distance to the data point on column n. The interpolation of intermediate pixels then takes place over vertical columns, rather than horizontal rows. This switch in interpolation direction keeps the interpolation distances small and the two interpolation data points relatively close together in range from the transducer, independent of the geometrical orientation of the scan line on the display. When the value of $|\phi|$ next becomes less than 45°, D(n) and V(n) are processed, and DP(n) and VP(n) are computed in the same manner as for $|\phi| < \text{or} = 45°$.

The scan conversion process takes place using one scan line at a time. For a handheld scanhead, the assumption is made that successive data lines are close to each other in space, and simple linear interpolation between data in the V(n) and VP(n) arrays is adequate for pixel filling. For relatively large movements between display lines, it may be possible to obtain better results by first employing interpolation schemes between the successive sampled data arrays S(n) and SP(n), to obtain intermediate echo data lines. These intermediate intensity data lines can be used in the same manner as actual data lines, by also interpolating the position information as well, and creating a complete new data structure which can be passed to the scan conversion module. For more sophisticated interpolation methods, it may be necessary to maintain data for more than just the previous scan line. For a three or four point interpolation over the sampled data, the scan conversion can run one or two lines behind the acquisition process, with three or four scan lines, along with the associated position information, maintained in a large memory buffer.

While the preferred embodiments of the invention have been illustrated and described, variations will be apparent to those skilled in the art. Accordingly, the scope of the invention is to be determined by reference to the following claims.

The embodiments of the invention in which an exclusive property or privilege is claimed are defined as follows:

1. A sensing system for producing sensor data for a subject and for determining the relative positions of scan points for which the sensor data is produced, the sensing system comprising:

signal acquisition means comprising scanning means having two or more ultrasound transducers, means for causing the scanning means to transmit pulses of ultrasound energy onto the subject as the scanning means is moved, whereby echoes backscattered from the subject are received by the scanning means, and means for converting said echoes into echo signals for each transducer;

sensing means for producing sensor data for the subject for a scan point having a known position with respect to the scanning means, whereby sensor data is produced at a series of scan points as the scanning means moves;

Doppler processing means for processing the echo signals to produce position data representing the positions of said series of scan points with respect to one another; and combining means for combining the sensor data and the position data to produce an indication of the variation of the sensor data with position.

2. The system of claim 1, wherein the Doppler processing means produces the position data by processing the echo signals from each transducer for each of two scan points located at different ranges along a scan line.

3. The system of claim 1, wherein said two or more ultrasound transducers comprise three transducers, wherein the Doppler processing means processes the echo signals from the three transducers to produce the position data, and wherein the position data represents translational movement of the scanning means in two dimensions and rotation of the scanning means in a plane defined by said two dimensions.

4. The system of claim 1, wherein said two or more ultrasound transducers comprise four transducers, wherein the Doppler processing means processes the echo signals from the four transducers to produce the position data, and wherein the position data represents translational movement of the scanning means in three dimensions and rotation of the scanning means in two dimensions.

5. The system of claim 1, wherein the sensing system comprises an ultrasound imaging system, wherein the sensing means comprises image processing means for processing one or more of the echo signals to produce intensity data for a scan line having a known orientation with respect to the scanning means, wherein the position data represents the relative positions of a series of scan lines, and wherein the combining means comprises scan conversion means for combining the intensity data and the position data to produce an image of the subject.

6. The system of claim 5, wherein the Doppler processing means produces the position data by processing the echo signals from each transducer for each of two range points located at different ranges along the scan line.

7. The system of claim 5, wherein said two or more ultrasound transducers comprise three transducers, wherein the Doppler processing means processes the echo signals from the three transducers to produce the position data.

8. The system of claim 7, wherein the position data represents translational movement of the scanhead in two dimensions and rotation of the scanhead in a plane defined by said two dimensions.

9. The system of claim 5, wherein said two or more ultrasound transducers comprise four transducers, wherein the Doppler processing means processes the echo signals from the four transducers to produce the position data.

10. The system of claim 9, wherein the position data represents translational movement of the scanning means in three dimensions and rotation of the scanning means in two dimensions.

11. The system of claim 5, wherein said two or more ultrasound transducers comprise a central transducer and a plurality of annular transducers concentrically positioned around the central transducer, and wherein the Doppler processing means processes the echo signals from the central transducer and one of the annular transducers to produce the position data.

12. The system of claim 11, wherein the Doppler processing means produces the position data by processing the echo signals from the central transducer and from said one annular transducer for each of two range points located at different ranges along the scan line, and wherein the image processing means produces the intensity data by processing the echo signals from all transducers.

13. The system of claim 5, wherein said two or more ultrasound transducers comprise an annular array of transducers comprising a central transducer and a plurality of annular transducers concentrically positioned around the central transducer, and first and second outer transducers positioned on opposite sides of the annular array of transducers, wherein the image processing means produces the intensity data by processing the echo signals from the annular array of transducers, and wherein the Doppler processing means produces the position data by processing the echo signals from the central transducer and the first and second outer transducers.

14. The system of claim 13, wherein the position data represents translational movement of the scanning means in two dimensions and rotation of the scanning means in a plane defined by said two dimensions, the central transducer and the outer transducers being located in said plane.

15. The system of claim 14, wherein the Doppler processing means produces the position data by processing the echo signals from the central transducer and outer transducers for each of two range points located at different ranges along the scan line.

16. The system of claim 5, wherein the scan conversion means comprises a general purpose computer.

17. The system of claim 5, wherein the image processing means comprises means for generating and processing the echo signals to produce intensity data for a plurality of sensing directions used for image formation, each direction having a known orientation with respect to the scanning means, wherein the Doppler processing means produces position data for the scanning means from a single scan direction and wherein the scan conversion means combines the intensity data and the position data to produce an image or collection of images representing a region of the subject.

18. A sensing method, comprising:
transmitting pulses of ultrasound energy into a subject;

receiving echoes of the transmitted pulses backscattered from the subject using a scanning means having two or more ultrasound transducers, to produce echo signals for each transducer;

producing sensor data for the subject for a scan point having a known position with respect to the scanning means;

processing the echo signals to produce position data representing the relative positions of a series of scan points; and combining the sensor data and the position data to produce an indication of the variation of the sensor data with position.

19. The method of claim 18, wherein the position data is produced by processing the echo signal from each of the transducers for each of two scan points located at different ranges along a scan line.

20. The method of claim 18, wherein the position date represents translational movement of the scanning means in two dimensions and rotation of the scanning means in a plane defined by the two dimensions.

21. The method of claim 18, wherein the position data represents translational movement of the scanning means in three dimensions and rotation of the scanning means in two dimensions.

22. The method of claim 18, wherein the step of producing sensor data comprises processing one or more of the echo signals to produce intensity data for a scan line having a known orientation with respect to the scanning means, and wherein the combining step comprises producing a two-dimensional image of the subject.

23. A scan conversion method for use in an ultrasound imaging system, for converting sample values at a plurality of sample points into pixel values at a plurality of pixels, the sample points lying along a plurality of scan lines, the pixels forming an array having two dimensions, each pixel having a coordinate along each dimension, the method comprising:

for each scan line, combining the sample values at the sample points lying along the scan line to produce intermediate values for the scan line at a plurality of intermediate points, each intermediate point having a coordinate along each dimension, a first coordinate of each intermediate point being equal to the corresponding coordinate of one of the pixels; and combining the intermediate values of adjacent scan lines to produce the pixel values.

24. The scan conversion method of claim 23, wherein for each pixel, the second combining step comprises combining intermediate values from intermediate points having equal first coordinates.

25. The scan conversion method of claim 24, wherein for each pixel, the second combining step further comprises combining intermediate values from first and second intermediate points having second coordinates respectively greater than and less than the second coordinate of the pixel.

26. The scan conversion method of claim 23, wherein for each intermediate point, the step of combining the sample values comprises combining sample values from first and second sample points having first coordinates respectively greater than and less than the first coordinate of the intermediate point.

27. The scan conversion method of claim 23, wherein for each scan line, the first coordinate is selected so as to maximize the number of intermediate points for the scan line.

* * * * *